US009662506B2

(12) United States Patent
Govea

(10) Patent No.: US 9,662,506 B2
(45) Date of Patent: May 30, 2017

(54) SYSTEMS AND METHODS FOR MAKING AND USING IMPROVED OPERATING-ROOM CABLES FOR ELECTRICAL STIMULATION SYSTEMS

(71) Applicant: BOSTON SCIENTIFIC NEUROMODULATION CORPORATION, Valencia, CA (US)

(72) Inventor: Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 345 days.

(21) Appl. No.: 14/330,330

(22) Filed: Jul. 14, 2014

(65) Prior Publication Data
US 2015/0025609 A1    Jan. 22, 2015

Related U.S. Application Data

(60) Provisional application No. 61/847,912, filed on Jul. 18, 2013.

(51) Int. Cl.
*A61N 1/375* (2006.01)
*A61N 1/05* (2006.01)
(52) U.S. Cl.
CPC ......... *A61N 1/3752* (2013.01); *A61N 1/0534* (2013.01); *A61N 1/0551* (2013.01)
(58) Field of Classification Search
CPC ............................ A61N 1/3752; A61N 1/0534
USPC .................................................. 607/117, 116
See application file for complete search history.

(56) References Cited

U.S. PATENT DOCUMENTS

| 5,354,326 | A | 10/1994 | Comben et al. |
| 5,782,892 | A | 7/1998 | Castle et al. |
| 5,931,861 | A | 8/1999 | Werner et al. |
| 6,038,479 | A | 3/2000 | Werner et al. |

(Continued)

FOREIGN PATENT DOCUMENTS

WO    2012/075497    6/2012

OTHER PUBLICATIONS

U.S. Appl. No. 14/962,938, filed Dec. 8, 2015.
U.S. Appl. No. 14/992,931, filed Jan. 11, 2016.

*Primary Examiner* — Christopher D Koharski
*Assistant Examiner* — Roland Dinga
(74) *Attorney, Agent, or Firm* — Lowe Graham Jones PLLC; Bruce E. Black

(57) ABSTRACT

An operating-room-cable assembly includes a lead connector with a lead-connector housing for receiving a lead. The lead-connector housing includes a first housing element and a second housing element that slide relative to one another to transition the lead-connector housing between an open position and a closed position. A connector port is defined in the lead-connector housing and includes a first surface formed by the first housing element and a second surface formed by the second housing element. A lead retainer is disposed along the second surface and receives the lead when the lead-connector housing is in the open position. Connector contacts are disposed along the first surface. The connector contacts couple to terminals disposed along the lead when the lead is received by the lead retainer and the lead-connector housing is in the closed position. Operating-room-cable conductors are coupled to the connector contacts and extend along the elongated body.

20 Claims, 9 Drawing Sheets

(56) References Cited

U.S. PATENT DOCUMENTS

| | | |
|---|---|---|
| 6,038,481 A | 3/2000 | Werner et al. |
| 6,181,969 B1 | 1/2001 | Gord |
| 6,192,278 B1 | 2/2001 | Werner et al. |
| 6,343,233 B1 | 1/2002 | Werner et al. |
| 6,397,108 B1 | 5/2002 | Camps et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,687,538 B1 | 2/2004 | Hrdlicka et al. |
| 6,741,892 B1 | 5/2004 | Meadows et al. |
| 6,950,709 B2 | 9/2005 | Baudino |
| 6,980,863 B2 | 12/2005 | van Venrooij et al. |
| 7,244,150 B1 | 7/2007 | Brase et al. |
| 7,437,193 B2 | 10/2008 | Parramon et al. |
| 7,493,159 B2 | 2/2009 | Hrdlicka et al. |
| 7,539,542 B1 | 5/2009 | Malinowski |
| 7,548,788 B2 | 6/2009 | Chinn et al. |
| 7,563,141 B2 | 7/2009 | Alexander et al. |
| 7,594,828 B2 | 9/2009 | Alexander et al. |
| 7,633,023 B1 | 12/2009 | Cappa et al. |
| 7,672,734 B2 | 3/2010 | Anderson et al. |
| 7,736,192 B2 | 6/2010 | Alexander et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,239,042 B2 | 8/2012 | Chinnn et al. |
| 8,364,278 B2 | 1/2013 | Pianca et al. |
| 8,401,670 B2 | 3/2013 | Mehdizadeh et al. |
| 8,849,396 B2 | 9/2014 | DeRohan et al. |
| 9,101,775 B2 | 8/2015 | Barker |
| 2003/0199948 A1 | 10/2003 | Kokones et al. |
| 2004/0106964 A1 | 6/2004 | Fischer, Sr. et al. |
| 2005/0165465 A1 | 7/2005 | Pianca et al. |
| 2006/0004419 A1* | 1/2006 | Olbertz ............... A61N 1/3752 607/37 |
| 2007/0150036 A1 | 6/2007 | Anderson |
| 2007/0197896 A1 | 8/2007 | Moll et al. |
| 2010/0070012 A1* | 3/2010 | Chinn ................ A61N 1/0553 607/152 |
| 2010/0106204 A1 | 4/2010 | Moffitt et al. |
| 2010/0249869 A1 | 9/2010 | Ries et al. |
| 2011/0098795 A1 | 4/2011 | Mehdizadeh et al. |
| 2011/0218549 A1 | 9/2011 | Barker |
| 2013/0098678 A1 | 4/2013 | Barker |

\* cited by examiner

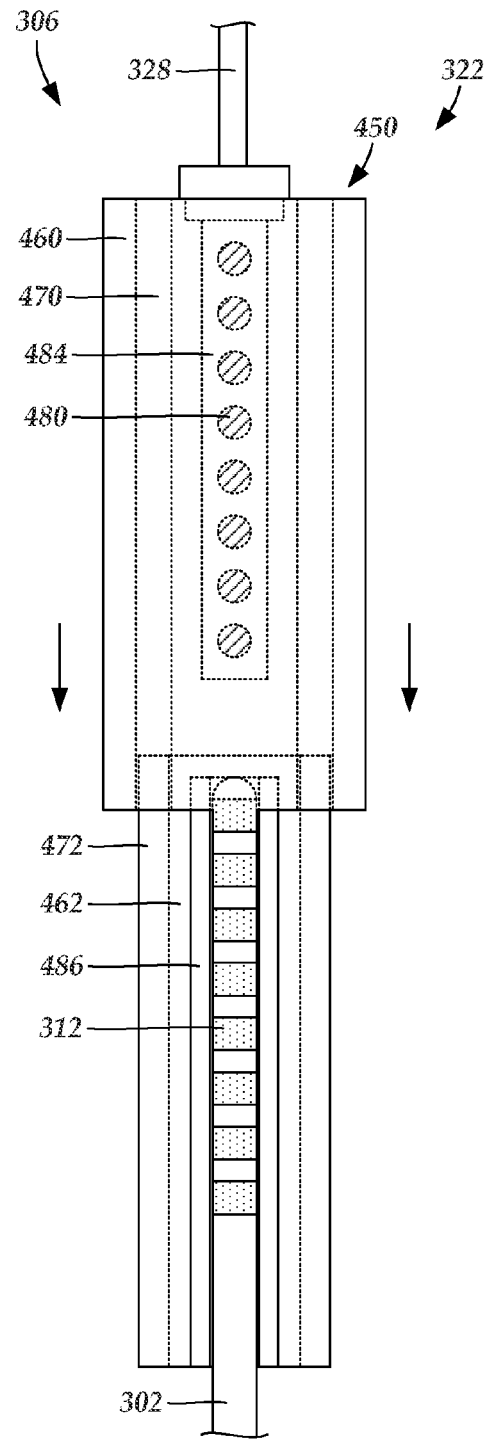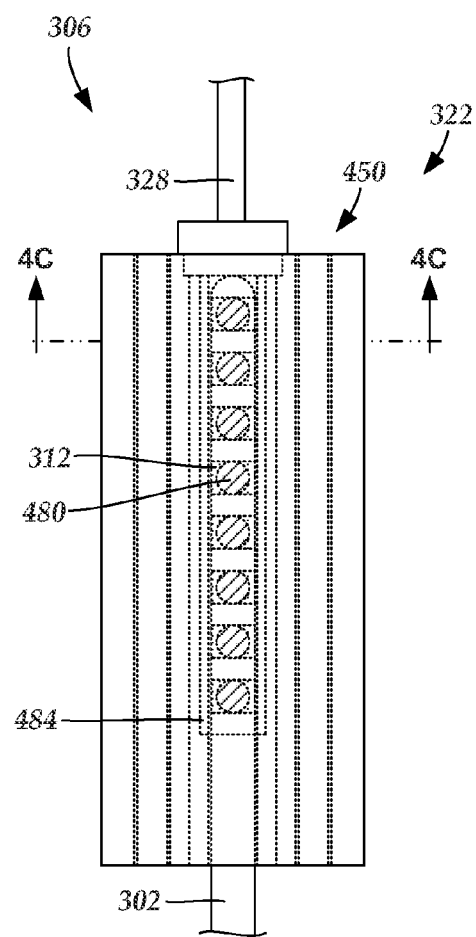
Fig. 5A
Fig. 5B

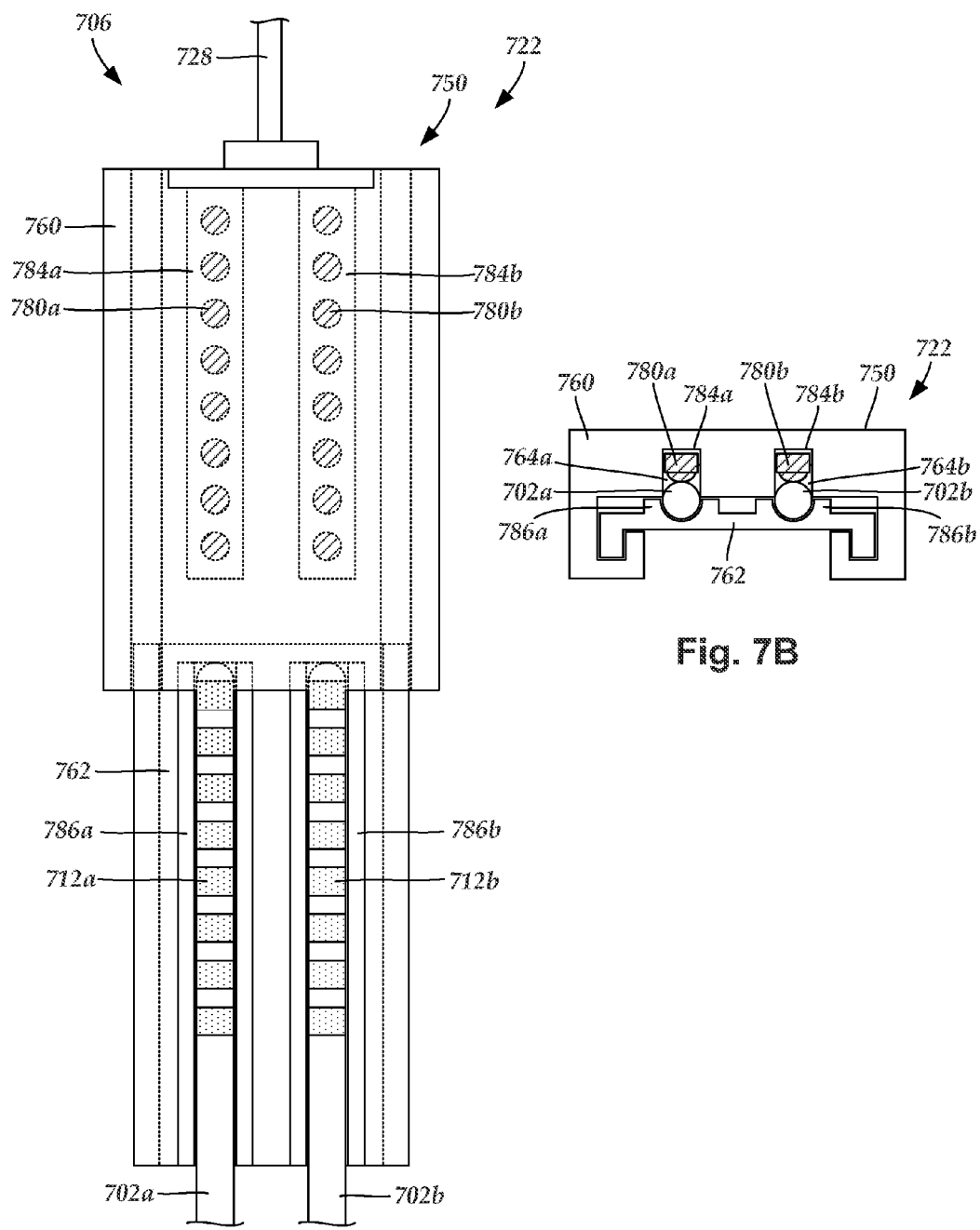

SYSTEMS AND METHODS FOR MAKING AND USING IMPROVED OPERATING-ROOM CABLES FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/847,912, filed Jul. 18, 2013, which is incorporated herein by reference.

FIELD

The present invention is directed to the area of implantable electrical stimulation systems and methods of making and using the systems. The present invention is also directed to implantable electrical stimulation systems that include operating-room cables suitable for use with deep brain stimulation systems, as well as methods of making and using the stimulation systems and operating-room cables.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an operating-room-cable assembly for electrically coupling at least one implantable electrical stimulation lead to a trial stimulator includes an elongated body having a first end portion and an opposing second end portion. A trial-stimulator connector is disposed along the second end portion of the elongated body. A lead connector is disposed along the first end portion of the elongated body and is electrically coupled to the trial-stimulator connector. The lead connector is configured and arranged to mechanically receive a proximal end portion of a first electrical stimulation lead. The lead connector includes a lead-connector housing having an interior and a longitudinal length. The lead-connector housing includes a first housing element and a second housing element that are slidably coupleable to one another along the longitudinal length of the lead-connector housing to transition the lead-connector housing between an open position and a closed position. A first connector port is defined along the interior of the lead-connector housing and extends along the longitudinal length of the lead-connector housing. The first connector port includes a first longitudinal surface formed by the first housing element and a second longitudinal surface formed by the second housing element. A first lead retainer is disposed along the second longitudinal surface of the first connector port and is open to the first connector port. The first lead retainer is configured and arranged to receive the proximal end portion of the first electrical stimulation lead when the lead-connector housing is in the open position. A first plurality of connector contacts is disposed along the first longitudinal surface of the first connector port and is open to the first connector port. The first plurality of connector contacts is configured and arranged to couple to the plurality of terminals disposed along the proximal end portion of the first electrical stimulation lead when the proximal end portion of the first electrical stimulation lead is received by the first lead retainer and the lead-connector housing is in the closed position. A plurality of operating-room-cable conductors is coupled to the first plurality of connector contacts and extends along the elongated body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic top view of one embodiment of the portion of the lead of FIG. 4B and the lead connector of FIG. 4B, where the lead connector includes a housing having a first housing element and a second housing element that is slidably coupleable with the first housing element, and where the housing in an open position and the lead is disposed on the second housing element, according to the invention;

FIG. 5B is a schematic top view of one embodiment of the portion of the lead of FIG. 5A disposed in a second housing element of a housing of the lead connector of FIG. 5A, where the second housing element has been slid relative to a first housing element of the housing to transition the housing into a closed position with the lead disposed inside the lead connector, according to the invention;

FIG. 7A is a schematic top view of one embodiment of proximal end portions of two leads and a lead connector, where the lead connector includes a housing having a first housing element and a second housing element that is slidably coupleable with the first housing element, and where the housing in an open position and the leads are disposed on the second housing element, according to the invention;

FIG. 7B is a schematic end view of one embodiment of the portions of the leads of FIG. 7A disposed in a second housing element of a housing of the lead connector of FIG. 7A, where the second housing element has been slid relative to a first housing element of the housing to transition the housing into a closed position with the leads disposed inside the lead connector, according to the invention.

DETAILED DESCRIPTION

The present invention is directed to the area of implantable electrical stimulation systems and methods of making and using the systems. The present invention is also directed to implantable electrical stimulation systems that include operating-room cables suitable for use with deep brain stimulation systems, as well as methods of making and using the stimulation systems and operating-room cables.

Suitable implantable electrical stimulation systems include, but are not limited to, at least one lead with one or more electrodes disposed along a distal end portion of the lead and one or more terminals disposed along the one or more proximal end portions of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
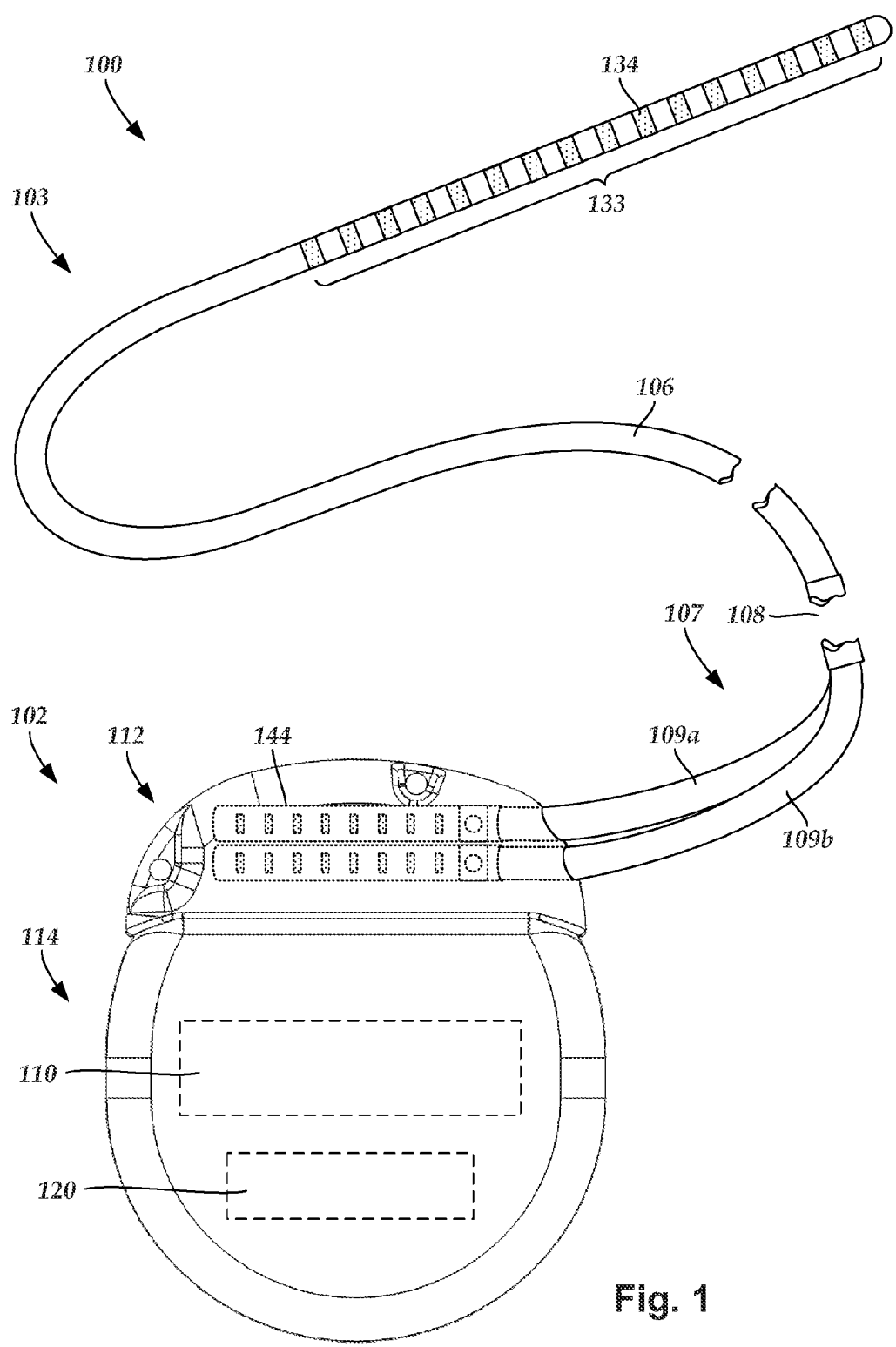
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIGS. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any suitable conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
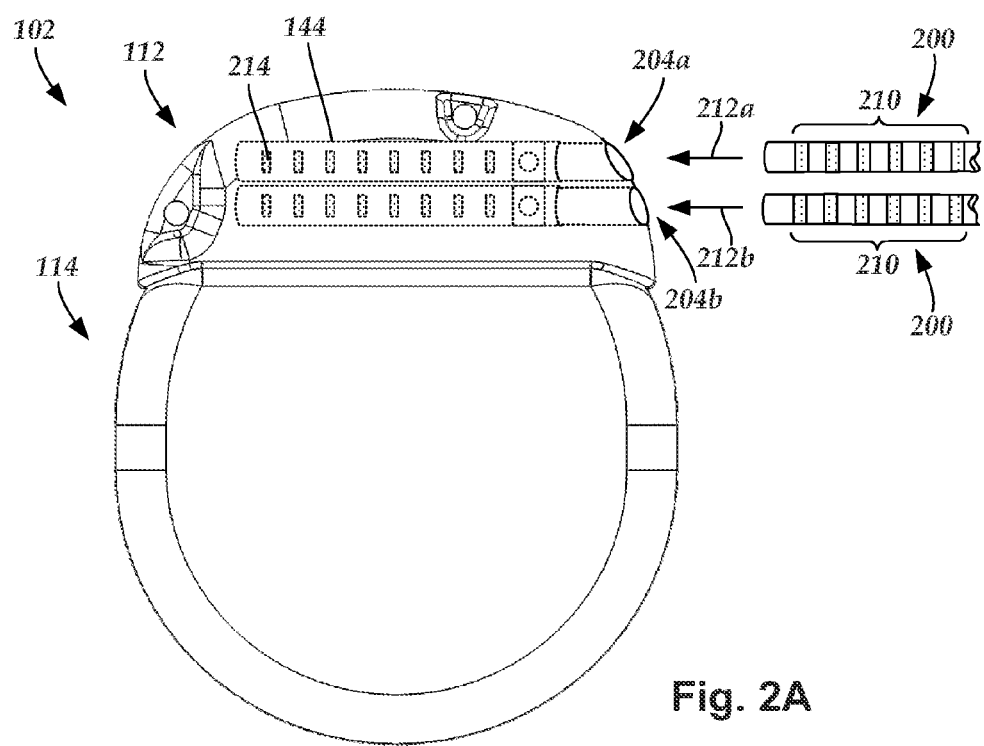
FIG. 2A is a schematic view of one embodiment of the control module of FIG. 1 configured and arranged to electrically couple to an elongated device, according to the invention.
Figure 2B:
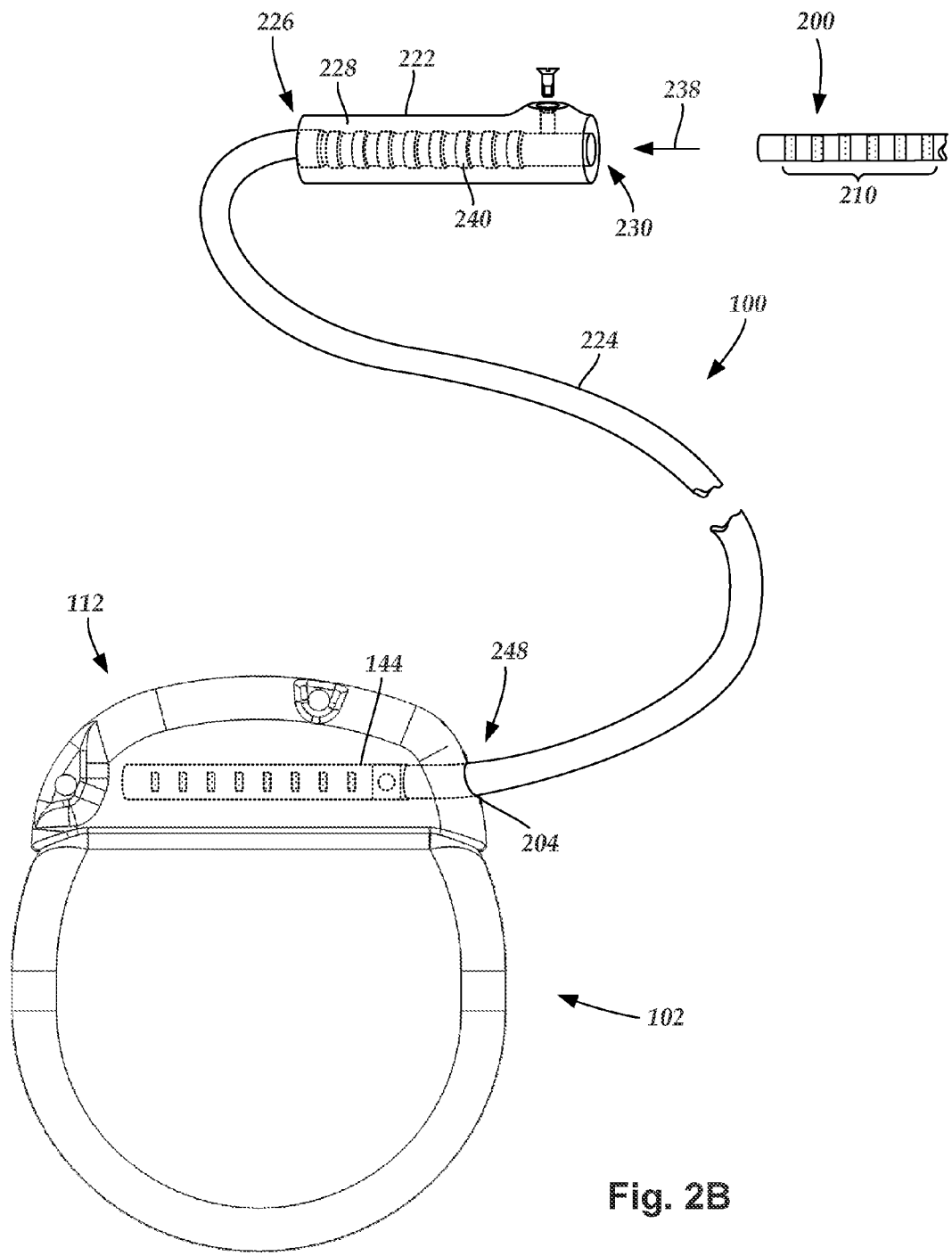
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 3:
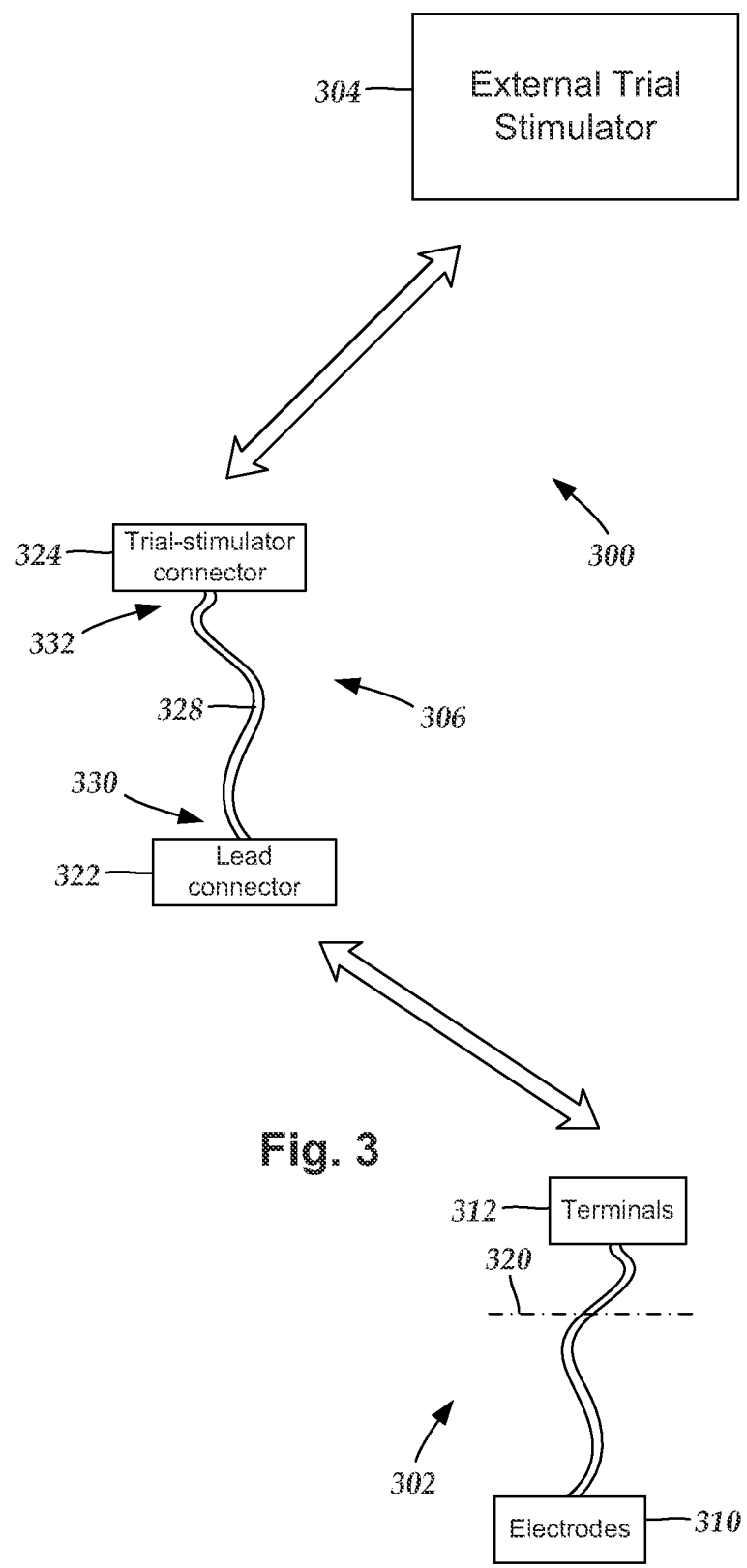
FIG. 3 is a schematic view of one embodiment of an operating-room cable for electrically coupling implanted lead electrodes to a trial stimulator, according to the invention.

Turning to FIG. 3, during implantation of the lead into a patient it is sometimes desirable to test the positioning or functionality of the electrodes within the patient prior to completion of the implantation. One way to test electrode positioning or functionality is to implant an electrode-including distal end portion of a lead (and, optionally, one or more lead extensions) into the patient. The proximal end portion of the lead (or lead extension) can then be electrically coupled to a trial stimulator that is disposed external to the patient to perform trial stimulations using the electrodes. Once it is determined that the electrodes are properly positioned and functioning within desired parameters, the trial stimulator can be removed from the proximal end portion of the lead (or lead extension) and replaced with an implantable control module, and the implantation can be completed.

The trial stimulations may continue for a short period (e.g., 7-10 days) where the patient is sent home with the lead, cable, and trial stimulator to assess the effectiveness of the therapy to determine if a permanent implanted system will be effective in treating the medical condition. During the trial stimulations, the lead can be electrically coupled to the trial stimulator by electrically coupling the proximal end portion of the lead (or lead extension) to an operating-room cable ("cable") which, in turn, is electrically coupled to the trial stimulator. In some cases, when multiple leads are implanted into a patient, multiple leads (or lead extensions) may be coupled to the cable.

FIG. 3 is a schematic view of one embodiment of a trial stimulation arrangement 300 that includes a lead 302, a trial stimulator 304, and an operating-room-cable assembly 306, that couples the lead 302 to the trial stimulator 304. The lead 302 includes an array of electrodes 310 and an array of terminals 312. The terminals 312 are configured and arranged to couple the electrodes 310 to the trial stimulator 304 when the operating-room-cable assembly 306 is coupled to each of the lead 302 and the trial stimulator 304.

During operation, the electrodes 310 are disposed internal to the patient, while the terminals 312 remain external to the patient, as shown in FIG. 3 by a line 320 schematically representing patient skin. Optionally, the trial stimulation arrangement 300 includes one or more additional devices (e.g., a lead extension, an operating-room cable extension, a splitter, an adaptor, or the like or combinations thereof).

The operating-room-cable assembly 306 includes an elongated body 328 having a first end portion 330 and an opposing second end portion 332, a lead connector 322, and a trial-stimulator connector 324. The lead connector 322 is disposed along the first end portion 330 of the operating-room-cable assembly 306 and is coupleable to the terminals 312 of the lead 302 (or lead extension). The trial-stimulator connector 324 is disposed along the second end portion 332 of the operating-room-cable assembly 306 and is coupleable to the trial stimulator 304, either directly or via one or more operating-room cable extensions.

Figure 4A:
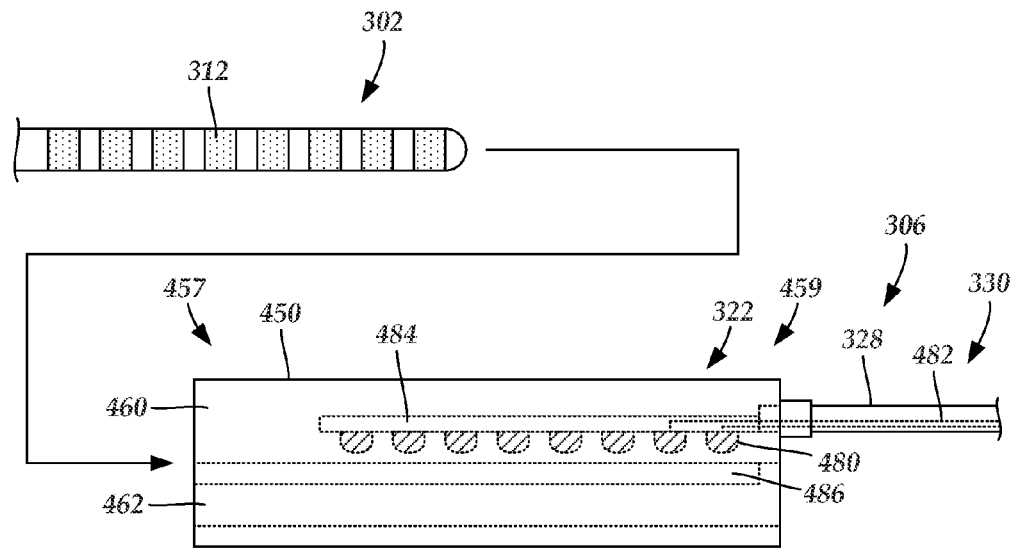
FIG. 4A is a schematic side view of one embodiment of a lead connector of an operating-room cable and a proximal end portion of a lead suitable for insertion into the lead connector, according to the invention.
Figure 4B:
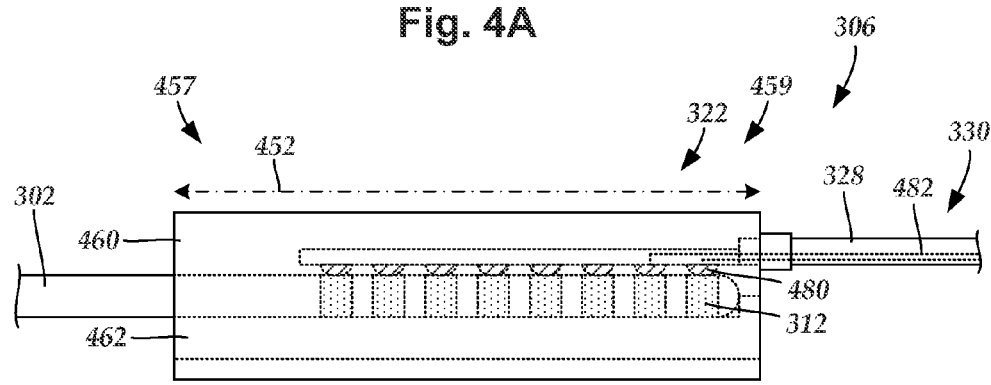
FIG. 4B is a schematic side view of one embodiment of the portion of the lead of FIG. 4A disposed in the lead connector of FIG. 4A, according to the invention.
Figure 4C:
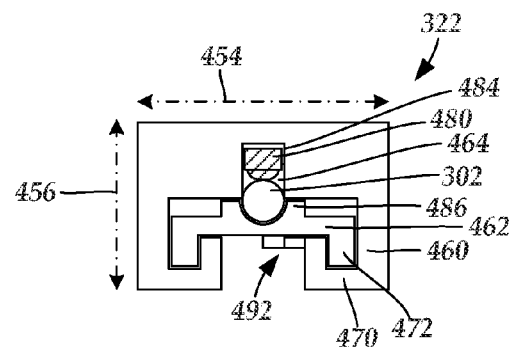
FIG. 4C is a schematic transverse cross-sectional view of one embodiment of the portion of the lead of FIG. 4B disposed in the lead connector of FIG. 4B, according to the invention.

Turning to FIGS. 4A-4C, at least some conventional operating-room-cable assemblies include lead connectors that are bulky or that have complicated or intricate retention mechanisms for coupling leads to the lead connectors. Bulky lead connectors may be difficult, or even impossible, to use at certain implantation sites. For example, a bulky lead connector may not be usable with stimulation systems implanted in the brain. Additionally bulky lead connectors may increase patient discomfort, as compared to less bulky connectors. Complicated or intricate retention mechanisms may increase procedure time from less complicated or intricate retention mechanisms, thereby increasing cost and potentially increasing patient discomfort associated with prolonged procedure times.

As described herein, an improved operating-room-cable assembly ("cable assembly") is disclosed that facilitates rapid and simple connection between a lead and the cable assembly. In at least some embodiments, the cable assembly includes a lead connector that is less bulky than at least some conventional cable-assembly lead connectors. In at least some embodiments, the cable assembly includes a retention mechanism for retaining leads that is more simple and less intricate than retention mechanisms of at least some conventional cable-assembly lead connectors. In at least some embodiments, the cable assembly is suitable for use in deep brain stimulation.

FIGS. 4A-4C illustrate schematically one embodiment of a portion of the cable assembly 306 and a proximal end portion of the lead 302. The portion of the cable assembly 306 shown in FIGS. 4A-4C includes the lead connector 322 and the first end portion 330 of the elongated member 328. The lead connector 322 is suitable for receiving the proximal end portion of a lead or lead extension, such as the proximal end of the lead 302, and electrically coupling terminals disposed along the lead or lead extension to the external trial stimulator 304.

FIG. 4A schematically illustrates, in side view, the proximal end portion of the lead 302 disposed external to the lead connector 322. FIG. 4B schematically illustrates, in side view, the proximal end portion of the lead 302 disposed in the lead connector 322. FIG. 4C schematically illustrates, in transverse cross-sectional view, the proximal end portion of the lead 302 disposed in the lead connector 322.

The lead connector 322 includes a lead-connector housing 450 having a longitudinal length 452, a transverse width 454, a transverse height 456, a first end 457, and an opposing second end 459. The lead-connector housing 450 has a first housing element 460 and a second housing element 462 that slides relative to the first housing element 460. In at least some embodiments, the second housing element 462 slides relative to the first housing element 460 along the longitudinal length 452 of the connector housing 450.

Connector contacts, such as connector contacts 480, and a lead retainer 486 are disposed in the lead-connector housing 450 such that the connector contacts 480 and the lead retainer 486 are disposed on different housing elements of the lead-connector housing 450. In at least some embodiments, the connector contacts 480 are disposed along the first housing element 460, while the lead retainer 486 is disposed along the second housing element 462. In at least some embodiments, the connector contacts 480 are disposed in the first housing element 460, while the second housing element 462 receives the lead 302 and slides relative to the first housing element to transition the lead-connector housing 450 between: an open position where the lead is insertable or removable from the lead-connector housing 450; and a closed position where the lead terminals are placed in contact with the connector contacts 480.

When the lead is inserted into the lead retainer 486 and the lead-connector housing 450 is transitioned to a closed position, the lead terminals are coupled (via the connector contacts 480) to operating-room-cable conductors 482 that extend along the elongated member 328 and that are coupleable with the external trial stimulator 304, via the trial-stimulator connector (324 in FIG. 3). For clarity of illustration, FIGS. 4A-4B show two operating-room-cable conductors 482 disposed within the cable assembly 306. It will be understood that any suitable number of conductors can be used. In some embodiments, the number of operating-room-cable conductors 482 is equal to the number of connector contacts 480 disposed in the lead connector 322. In other embodiments, the number of operating-room-cable conductors 482 is either less than or greater than the number of connector contacts 480 disposed in the lead connector 322.

In at least some embodiments, the elongated member 328 is coupled to the second end 459 of the lead-connector housing 450. In at least some embodiments, the elongated member 328 is coupled directly to the housing element of the lead-connector housing 450 within which the connector contacts 480 are disposed. In at least some embodiments, the elongated member 328 is coupled directly to the first housing element 460.

The slidably-coupled first and second housing elements 460 and 462 form a lead connector port 464 along an interior of the lead-connector housing 450 that opens along the first end 457 of the lead-connector housing 450 and that is suitable for receiving the lead. The lead connector port 464 includes a first longitudinal surface formed by the first housing element 460 and a second longitudinal surface formed by the second housing element 462. In at least some embodiments, the connector contacts 480 are disposed along the first longitudinal surface. In at least some embodiments, the lead retainer is disposed along the second longitudinal surface. The connector contacts 480 and the lead retainer 486 are both open to the lead connector port 464 and are adapted for retaining the lead in the lead connector port 464 such that the lead terminals couple with the connector contacts 480. In some embodiments, the lead connector port 464 has ridges, threads, and grooves to secure the lead within the lead connector port 464.

Any suitable number of connector contacts 480 can be disposed in the lead connector 322 including, for example, one, two, three, four, five, six, seven, eight, nine, ten, eleven, twelve, thirteen, fourteen, fifteen, sixteen, twenty, twenty-four, twenty-eight, thirty-two, or more connector contacts 480. In at least some embodiments, the number of connector contacts is equal to the number of terminals disposed along the lead or lead extension. As explained in more detail below with reference to FIGS. 7A-7B, in at least some embodiments the lead connector 322 is configured and arranged to receive multiple leads. In which case, the total number of connector contacts disposed in the lead connector may exceed the number of terminals disposed along any particular lead. In at least some embodiments, the total number of connector contacts disposed in the lead connector may be equal to the number of terminals disposed along the lead multiplied by the number of leads that the lead connector is configured to receive.

Optionally, the connector contacts 480 are disposed along an elongated support member 484 disposed in the lead-connector housing 450. In at least some embodiments, the support member 484 extends along the longitudinal length 452 of the lead-connector housing 450. The elongated support member 484 may provide a rigid support that holds the connector contacts 480 in position to couple with the lead terminals when the lead is inserted into the lead retainer 486 and the lead-connector housing 450 is transitioned to a closed position.

The lead retainer 486 is configured to receive the proximal end portion of the lead (or lead extension) and removably retain the lead (or lead extension) within the lead connector 322. In at least some embodiments, the lead retainer 486 removably retains the lead such that the received portion of the lead does not move relative to the lead retainer 486 without application of an external force (e.g., by a user) to remove the lead from the lead retainer 486.

The first and second housing elements 460 and 462 can slide relative to one another in any suitable manner. In and least some embodiments, the first housing element 460 and the second housing element 462 have interlocking rails (e.g., one or more first rails 470 and one or more second rails 472) that enable the second housing element 462 to slide relative to the first housing element 460. In some embodiments, the one or more first rails 470 are disposed on the first housing element 460 and the one or more second rails 472 are disposed on the second housing element 462. In FIG. 4C, two first rails 470 are shown disposed on the first housing element 460 and two second rails 472 are shown disposed on the second housing element 462. Other numbers of interlocking rails 470, 472 are contemplated.

In at least some embodiments, the one or more first rails 470 include a track, groove, channel, or duct. In at least some embodiments, the one or more first rails 470 include ribs, threads, or other suitable pattern configured for facilitating retention between the interlocking rails 470, 472 or facilitating retention of the rails 470, 472 to their respective housing elements 460, 462. In at least some embodiments, the second rail 472 includes one or more members that extend from the second housing element 462 and that interlock with a track formed along the first rail 470.

Optionally, the lead-connector housing 450 includes a locking assembly 492 for temporarily preventing the second housing element 462 from sliding relative to the first housing element 460. The locking assembly 492 is partially disposed along the first housing element 460 and partially disposed along the second housing element 462. In some embodiments, the locking assembly 492 is configured to lock the lead-connector housing 450 in a closed position. In other embodiments, the locking assembly 492 is configured to lock the lead-connector housing 450 in an open position. In at least some embodiments, the locking assembly 492 is configured and arranged to lock the received lead within the lead-connector housing 450 of the lead connector 322, thereby mechanically locking the lead to the operating-room-cable assembly 306.

The locking assembly 492 can be implemented using any suitable temporary engaging features disposed on or in the housing elements 460, 462 (e.g., a latch mechanism, a hook mechanism, a snap mechanism, a tab-and-slot mechanism, or the like or combinations thereof). In some instances, a portion of the locking assembly 492 includes teeth that are configured to engage with another portion of the locking assembly 492.

FIG. 5A schematically illustrates, in top view, one embodiment of the lead-connector housing 450 in an open position. The lead 302 is disposed on the lead retainer 486 of the second housing element 462. FIG. 5B schematically illustrates, in top view, one embodiment of the lead-connector housing 450 transitioned to a closed position. As shown in FIG. 5B, when the lead 302 is disposed in the lead retainer 486 and the lead retainer housing 450 is transitioned to a closed position, the terminals 312 disposed along the lead 302 align with, and couple to, the connector contacts 480 disposed in the first housing element 460.

Figure 6A:
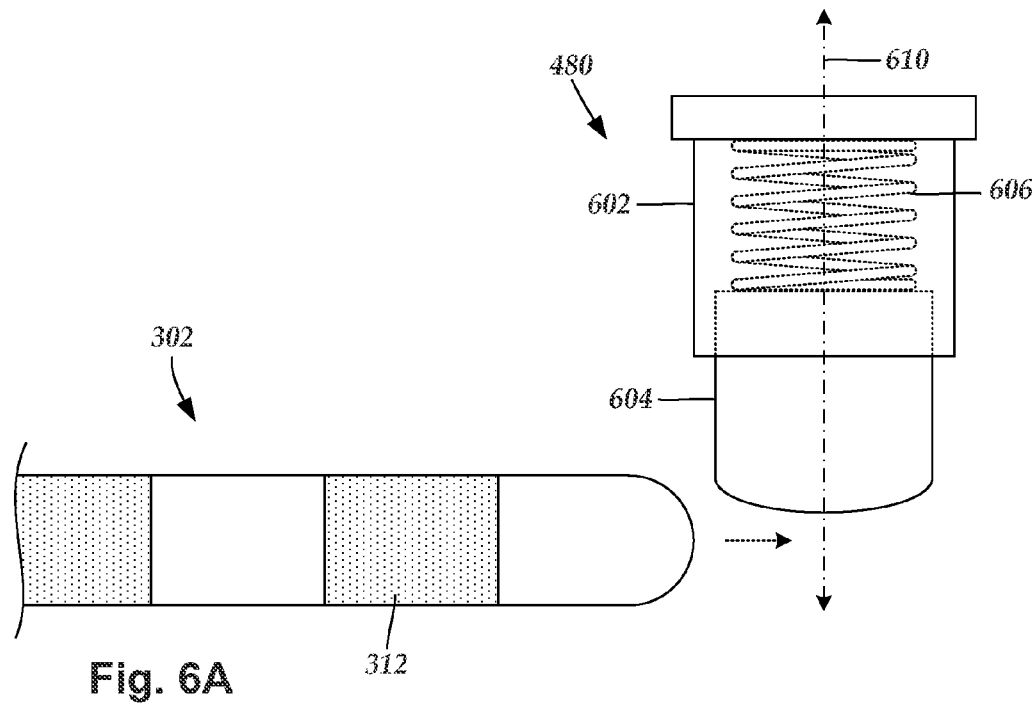
FIG. 6A is a schematic side view of one embodiment of a proximal end portion of the lead of FIG. 4A and a connector contact suitable for disposing in the lead connector of FIG. 4A and for coupling with terminals disposed on the lead, the connector contact including a biasing element in a relaxed position, according to the invention.
Figure 6B:
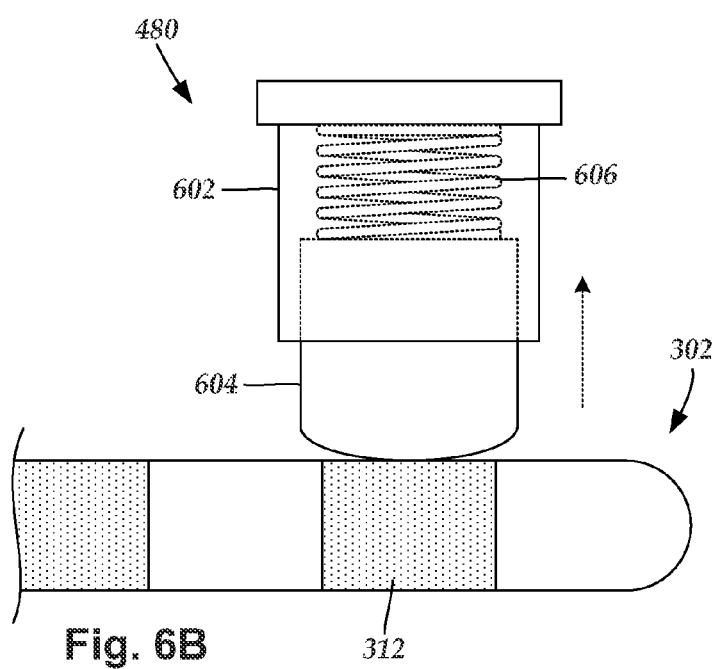
FIG. 6B is a schematic side view of one embodiment of the connector contact of FIG. 6A physically contacting a terminal disposed along a proximal end portion of the lead of FIG. 4A, the connector contact including a biasing element in a compressed position, according to the invention.

Turning to FIGS. 6A-6B, in at least some embodiments the connector contacts 480 are formed as spring contact probes. FIG. 6A is a schematic side view of one embodiment of the connector contact 480 and the proximal end portion of the lead 302 in proximity to the connector contact 480. FIG. 6B is a schematic side view of one embodiment of one of the terminals 312 disposed along the lead 302 physically contacting the connector contact 480. Note that in FIGS. 6A-6B the connector contact 480 is shown in an exaggerated size, for clarity of illustration.

The spring contact probes 480 each include a contact housing 602 and a spring-loaded pin 604 that is formed from a conductive material and that is configured and arranged to couple with a terminal (e.g., of the lead 302, or a lead extension, or the like). The spring contact probes 480 can be formed, either completely or in part (e.g., coated), using any conductive material suitable for implantation including, for example, Nitinol, stainless steel (e.g., 316L, or the like), platinum iridium, or the like.

In at least some embodiments, the spring-loaded pin 604 is electrically coupled to one or more of the operating-room-cable conductors (482 in FIGS. 4A-4B). When the spring-loaded pin 604 is electrically coupled to one or more of the operating-room-cable conductors, the operating-room-cable conductors can be directly coupled to the spring-loaded pin 604, or the elongated conductors can be coupled to the spring-loaded pin 604 via one or more of the contact housing 602, the support element (484 in FIGS. 4A-4C) or the biasing element 606 (described below).

In at least some embodiments, a biasing element (e.g., one or more coiled springs, one or more leaf springs, one or more elastomeric materials, or the like) 606 is disposed in the contact housing 602 and is coupled to the spring-loaded pin 604. The biasing element 606 is configured and arranged to compress or expand between a relaxed position (see e.g., FIG. 6A) and a compressed position (see e.g., FIG. 6B). The biasing element 606 is coupled to the spring-loaded pin 604 such that compression or expansion of the biasing element 606 causes a corresponding movement of the spring-loaded pin 604 along a spring axis 610. In at least some embodiments, the spring axis 610 is parallel to the height 456 of the connector housing 450. In at least some embodiments, when the spring contact probe 480 is in a relaxed position, at least a portion of the spring-loaded pin 604 extends into the lead-connector port (464 in FIG. 4C).

As shown in FIG. 6B, the spring-loaded pins 604 are configured and arranged such that at least a portion of the spring-loaded pins 604 retract, at least partially, into the contact housing 602 upon application of a force against the spring-loaded pins 604 along an axis transverse (or substantially transverse) to the spring axis 610. While retracted, the spring-loaded pins 604 continuously apply a force in the direction opposite to the direction of retraction along the spring axis 610. Thus, when the force applied to the spring-loaded pins 604 is removed, the retracted spring-loaded pins 604 return to their relaxed position with at least a portion of the spring-loaded pins 604 extending into the lead-connector port (464 in FIG. 4C).

When, as shown in FIG. 6B, the lead 302 is inserted into the lead-connector housing 450, the lead 302 exerts a force on the spring-loaded pins 604 that causes the spring-loaded pins 604 to retract. While retracted, the spring-loaded pins 604 continuously apply a force against the surface of the inserted lead 302, thereby maintaining mechanical contact with the lead 302. In at least some embodiments, when the lead 302 is operationally inserted into the lead-connector housing 450, the spring-loaded pins 604 align with the terminals 312 of the lead 302. In which case, the force applied against the terminals 312 by the refracted spring-loaded pins 604 forms (and maintains) an electrical connection between the operating-room-cable conductors (482 in FIGS. 4A-4B) and the inserted lead 302.

Optionally, the spring contact probes 480 can incorporate an actuator (e.g., a button, a lever, or the like) to control how far the spring-loaded probes 480 extend into the lead connector port (464 in FIG. 4C) of the lead-connector housing 450 when the spring-loaded pins 604 are in a relaxed position. In at least some embodiment, the actuator can be actuated, either manually or automatically, to pull the spring-loaded pins 604 away from the lead connector port (464 in FIG. 4C) prior to insertion of the lead 302. Pulling the spring-loaded pins 304 away from the lead connector port (464 in FIG. 4C) may reduce friction and insertion forces during the transition of the lead-connector housing 450 from an open position to a closed position. In at least some embodiments, the actuator automatically returns the spring-loaded pins 604 to their relaxed position after a set amount of time. In at least some other embodiments, the spring-loaded pins 604 are returned to their relaxed positions upon re-actuation of the actuator.

In at least some embodiments, the lead-connector housing 450 is configured to receive multiple leads. FIG. 7A schematically illustrates, in top view, one embodiment of proximal end portions of two leads 702a, 702b and a cable assembly 706. FIG. 7B schematically illustrates, in transverse cross-sectional view, one embodiment of the portions of the leads 702a, 702b and the cable assembly 706. The cable assembly 706 includes a lead connector 722 and an elongated body 728. The lead connector 722 includes a lead-connector housing 750 having a first housing element 760 and a second housing element 762 that slides relative to the first housing element 760 to transition the lead-connector housing 750 between an open position and a closed position.

As shown in FIGS. 7A-7B, in at least some embodiments a first set of connector contacts 780a and a second set of connector contacts 780b are disposed along the first housing element 760. The first set of connector contacts 780a is, optionally, disposed along a first elongated support element 784a and the second set of connector contacts 780a is, optionally, disposed along a second elongated support element 784b.

As also shown in FIGS. 7A-7B, the proximal end portion of the first lead 702a is positioned upon a first lead retainer 786a and the proximal end portion of the second lead 702b is positioned upon a second lead retainer 786b. The first set of connector contacts 780a and the first lead retainer 786a are each open to a first lead connector port 764a, and the second set of connector contacts 780b and the second lead retainer 786b are each open to a second lead connector port 764b.

In FIG. 7A, the proximal end portions of the leads 702a and 702b are shown positioned on the lead retainers 786a and 786b, respectively, while the lead-connector housing 750 is in an open position. As shown in FIG. 7A, the lead 702a (and the lead retainer 786a) is aligned with the connector contacts 780a, and the lead 702b (and the lead retainer 786b) is aligned with the connector contacts 780b such that terminals 712a disposed along the lead 702a couple with the connector contacts 780a and terminals 712b disposed along the lead 702b couple with the connector contacts 780b when the lead-connector housing 750 is transitioned to a closed position. FIG. 7B shows the lead-connector housing once the lead-connector housing 750 is transitioned to the closed position.

In FIGS. 7A-7B, the lead-connector housing 750 is shown configured and arranged to receive two leads. It will be understood that the lead-connector housing 750 can be configured to receive any suitable number of leads including one, two, three, four, five, six, seven, eight, or more leads. It will also be understood that, with reference to FIGS. 3-7B, the lead connector is configured to receive the proximal end portion of one or more leads. Alternately, the lead connector can be configured to receive the proximal end portions of one or more lead extensions, splitters, adaptors, or the like or combinations thereof in lieu of, or in addition to, receiving one or more leads.

Figure 8:
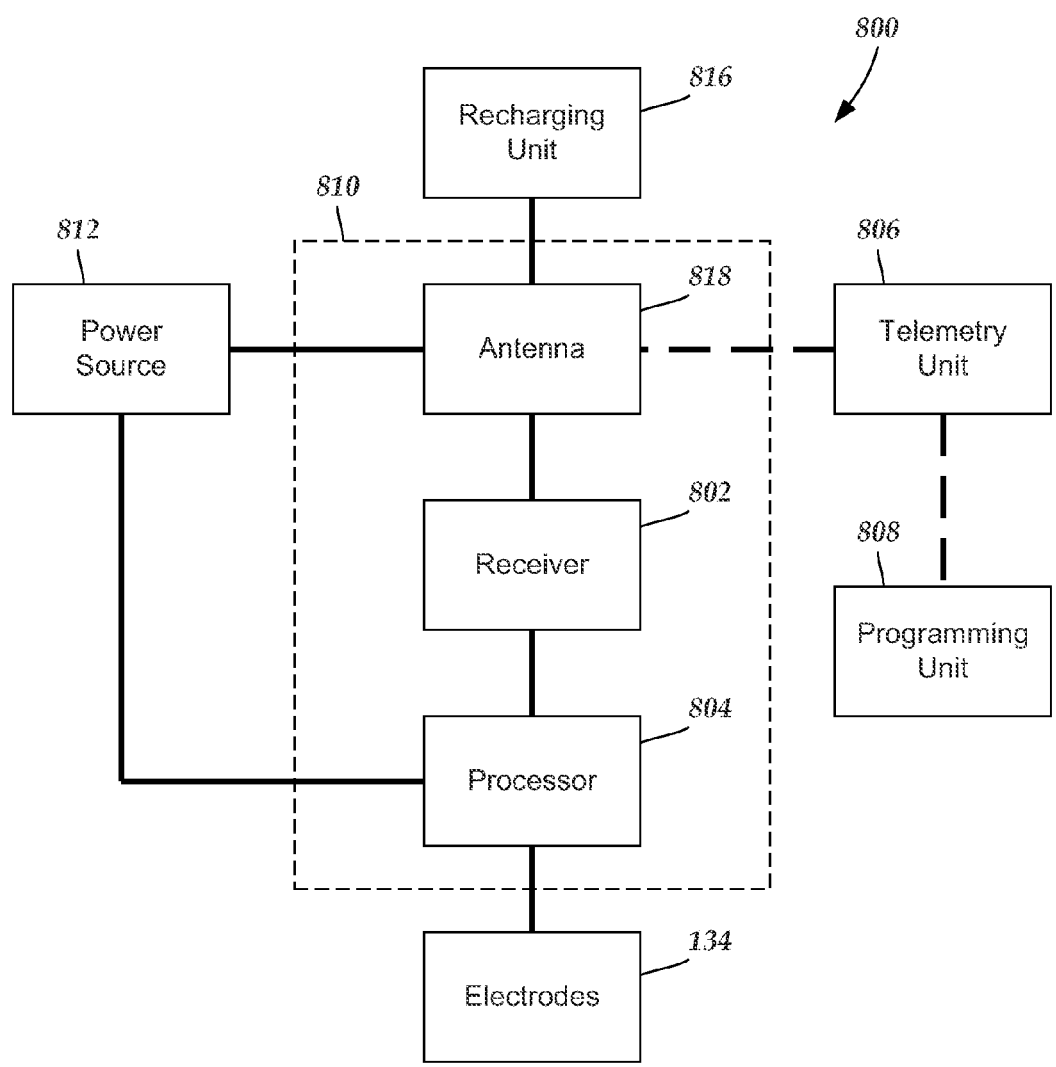
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An operating-room-cable assembly for electrically coupling at least one implantable electrical stimulation lead to a trial stimulator, the operating-room-cable assembly comprising:
   an elongated body having a first end portion and an opposing second end portion;
   a trial-stimulator connector disposed along the second end portion of the elongated body; and
   a lead connector disposed along the first end portion of the elongated body and electrically coupled to the trial-stimulator connector, the lead connector configured and arranged to mechanically receive a proximal end portion of a first electrical stimulation lead, the lead connector comprising
      a lead-connector housing having an interior and a longitudinal length, the lead-connector housing comprising a first housing element and a second housing element that are slidably coupleable to one another along the longitudinal length of the lead-connector housing to transition the lead-connector housing between an open position and a closed position by sliding one of the first housing element or second housing element longitudinally with respect to another of the first housing element or second housing element,
      a first connector port defined along the interior of the lead-connector housing and extending longitudinally along the longitudinal length of the lead-connector housing, the first connector port comprising a first longitudinal surface formed by the first housing element and a second longitudinal surface formed by the second housing element,
      a first lead retainer disposed along the second longitudinal surface of the first connector port and open to the first connector port, the first lead retainer configured and arranged to receive the proximal end portion of the first electrical stimulation lead when the lead-connector housing is in the open position, and
      a first plurality of connector contacts disposed along the first longitudinal surface of the first connector port and open to the first connector port, the first plurality of connector contacts configured and arranged to couple to a plurality of terminals disposed along the proximal end portion of the first electrical stimulation lead when the proximal end portion of the first electrical stimulation lead is received by the first lead retainer and the lead-connector housing is in the closed position; and a plurality of operating-room-cable conductors coupled to the first plurality of connector contacts and extending along the elongated body.

2. The operating-room-cable assembly of claim 1, wherein the first plurality of connector contacts comprises a plurality of spring contact probes.

3. The operating-room-cable assembly of claim 1, wherein the lead connector further comprises a first elongated support member disposed along the first housing element, and wherein the first plurality of connector contacts are coupled to the first elongated support member.

4. The operating-room-cable assembly of claim 3, wherein the first elongated support member extends longitudinally along the longitudinal length of the lead-connector housing.

5. The operating-room-cable assembly of claim 1, wherein the first housing element comprises at least one first rail that extends longitudinally along the longitudinal length of the lead-connector housing and the second housing element comprises at least one second rail that extends longitudinally along the longitudinal length of the lead-connector housing, and wherein the at least one first rail interlocks with the at least one second rail.

6. A method for performing a trial stimulation on a patient, the method comprising:

providing the operating-room-cable assembly of claim 1;

advancing a distal end portion of a first electrical stimulation lead into the patient with a proximal end portion of the first electrical stimulation lead extending outward from the patient, wherein the distal end portion of the first electrical stimulation lead is advanced to a position where a plurality of electrodes disposed along the distal end portion of the first electrical stimulation lead are in proximity to a target stimulation location;

placing the proximal end portion of the first electrical stimulation lead onto the first lead retainer of the lead-connector housing of the operating-room-cable assembly while the connector housing is in an open position;

sliding the first housing element of the lead-connector housing relative to the second housing element of the lead-connector housing to transition the lead-connector housing to a closed position and to electrically couple a plurality of terminals that are disposed along the proximal end portion of the first electrical stimulation lead and that are electrically coupled to the plurality of electrodes to the first plurality of connector contacts disposed in the connector housing; and electrically coupling the trial-stimulator connector of the operating-room-cable assembly to a trial stimulator.

7. An operating-room-cable assembly for electrically coupling at least one implantable electrical stimulation lead to a trial stimulator, the operating-room-cable assembly comprising:

an elongated body having a first end portion and an opposing second end portion;

a trial-stimulator connector disposed along the second end portion of the elongated body; and a lead connector disposed along the first end portion of the elongated body and electrically coupled to the trial-stimulator connector, the lead connector configured and arranged to mechanically receive a proximal end portion of a first electrical stimulation lead, the lead connector comprising a lead-connector housing having an interior and a longitudinal length, the lead-connector housing comprising a first housing element and a second housing element that are slidably coupleable to one another along the longitudinal length of the lead-connector housing to transition the lead-connector housing between an open position and a closed position, wherein the first housing element comprises at least one first rail that extends along the longitudinal length of the lead-connector housing and the second housing element comprises at least one second rail that extends along the longitudinal length of the lead-connector housing, and wherein the at last one first rail interlocks with the at least one second rail, wherein the at least one first rail is configured and arranged to slide relative the at least one second rail when the lead-connector housing transitions between an open position and a closed position, a first connector port defined along the interior of the lead-connector housing and extending along the longitudinal length of the lead-connector housing, the first connector port comprising a first longitudinal surface formed by the first housing element and a second longitudinal surface formed by the second housing element, a first lead retainer disposed along the second longitudinal surface of the first connector port and open to the first connector port, the first lead retainer configured and arranged to receive the proximal end portion of the first electrical stimulation lead when the lead-connector housing is in the open position, and a first plurality of connector contacts disposed along the first longitudinal surface of the first connector port and open to the first connector port, the first plurality of connector contacts configured and arranged to couple to a plurality of terminals disposed along the proximal end portion of the first electrical stimulation lead when the proximal end portion of the first electrical stimulation lead is received by the first lead retainer and the lead-connector housing is in the closed position; and a plurality of operating-room-cable conductors coupled to the first plurality of connector contacts and extending along the elongated body.

8. The operating-room-cable assembly of claim 1, wherein the elongated body is coupled to the lead connector along the first housing element of the lead-connector housing.

9. The operating-room-cable assembly of claim 1, wherein the lead connector further comprises a locking assembly partially disposed on the first housing element and partially disposed on the second housing element, the locking assembly configured and arranged to removably lock the lead-connector housing when the lead-connector housing in the open position.

10. The operating-room-cable assembly of claim 1, wherein the lead connector further comprises a locking assembly partially disposed on the first housing element and partially disposed on the second housing element, the locking assembly configured and arranged to removably lock the lead-connector housing when the lead-connector housing in the closed position.

11. The operating-room-cable assembly of claim 1, wherein the lead-connector housing further defines a second connector port along the interior of the lead-connector housing, the second connector port extending longitudinally along the longitudinal length of the lead-connector housing.

12. The operating-room-cable assembly of claim 11, wherein the second connector port comprises a first longitudinal surface formed by the first housing element and a second longitudinal surface formed by the second housing element.

13. The operating-room-cable assembly of claim 12, wherein the lead-connector housing further comprises a second lead retainer that is disposed along the second longitudinal surface of the second connector port and that is open to the second connector port, the second lead retainer configured and arranged to receive a proximal end portion of a second electrical stimulation lead when the connector housing is in the open position.

14. The operating-room-cable assembly of claim 13, wherein and the first lead retainer is configured and arranged to receive the proximal end portion of the first electrical stimulation lead and the second lead retainer is configured and arranged to receive the proximal end portion of the second electrical stimulation lead simultaneously with one another.

15. The operating-room-cable assembly of claim 13, wherein the lead-connector housing further comprises a second plurality of connector contacts that are disposed along the first longitudinal surface of the second connector port and that are open to the second connector port, the second plurality of connector contacts configured and arranged to couple to the plurality of terminals disposed along the proximal end portion of the second electrical stimulation lead when the proximal end portion of the second electrical stimulation lead is received by the second lead retainer and the lead-connector housing is in the closed position.

16. The operating-room-cable assembly of claim 15, wherein the lead connector further comprises a second elongated support member disposed along the first housing element, and wherein the second plurality of connector contacts are coupled to the second elongated support member.

17. The operating-room-cable assembly of claim 16, wherein the second elongated support member extends longitudinally along the longitudinal length of the lead-connector housing.

18. An insertion kit comprising:
the operating-room-cable assembly of claim 1; and
a first electrical stimulation lead having a distal end portion and a proximal end portion, the first electrical stimulation lead comprising
a plurality of electrodes disposed along the distal end portion of the first electrical stimulation lead,
a plurality of terminals disposed along the proximal end portion of the first electrical stimulation lead, and
a plurality of conductors, each conductor electrically coupling at least one of the plurality of electrodes to at least one of the plurality of terminals,
wherein the proximal end portion of the first electrical stimulation lead is insertable into the lead-connector housing of the operating-room-cable assembly.

19. The insertion kit of claim 18, further comprising a second electrical stimulation lead configured and arranged for inserting into the lead-connector housing of the operating-room-cable assembly simultaneously with the first electrical stimulation lead.

20. A trial stimulation arrangement for an electrical stimulation system, the trial stimulation arrangement comprising:
the insertion kit of claim 18, and
a trial stimulator configured and arranged to generate electrical stimulation signals, the trial stimulator disposed external to a patient and coupleable to the trial-stimulator connector of the operating-room-cable assembly of the insertion kit.

* * * * *